United States Patent

Carpentier et al.

[11] Patent Number: 5,814,100
[45] Date of Patent: Sep. 29, 1998

[54] MECHANICAL PROSTHETIC VALVE, AND METHODS OF ITS CONSTRUCTION AND OPERATION

[75] Inventors: Alain Carpentier, Paris, France; George X. Guo, Dove Canyon; Stefan G. Schreck, Vista, both of Calif.

[73] Assignee: Baxter International Inc., Deerfield, Ill.

[21] Appl. No.: 694,580

[22] Filed: Aug. 9, 1996

[30] Foreign Application Priority Data

Feb. 20, 1996 [FR] France ................................. 96 02052

[51] Int. Cl.⁶ ......................................... A61F 2/24
[52] U.S. Cl. .................................................. 623/2
[58] Field of Search .................. 623/2, 900; 137/512, 137/514, 533.11

[56] References Cited

U.S. PATENT DOCUMENTS

| | | |
|---|---|---|
| Re. 30,507 | 2/1981 | Kaster . |
| 3,370,305 | 2/1968 | Goott et al. . |
| 3,959,827 | 6/1976 | Kaster . |
| 3,974,854 | 8/1976 | Kurpanek . |
| 4,245,358 | 1/1981 | Moasser . |
| 4,276,658 | 7/1981 | Hanson et al. . |
| 4,417,360 | 11/1983 | Moasser . |
| 4,605,408 | 8/1986 | Carpentier . |
| 4,657,545 | 4/1987 | Zibelin . |
| 4,661,107 | 4/1987 | Fink . |
| 4,769,032 | 9/1988 | Steinberg . |
| 4,820,299 | 4/1989 | Phillippe et al. . |
| 4,863,460 | 9/1989 | Magladry . |
| 4,979,955 | 12/1990 | Smith . |
| 5,045,298 | 9/1991 | Muramatsu et al. . |
| 5,123,918 | 6/1992 | Perrier et al. . |
| 5,135,538 | 8/1992 | Pawlak et al. . |

FOREIGN PATENT DOCUMENTS

| | | |
|---|---|---|
| 0 023 797 | 2/1981 | European Pat. Off. . |
| 0 113 681 A1 | 7/1984 | European Pat. Off. . |
| 121 473A | 10/1984 | European Pat. Off. . |
| 0 220 097 | 4/1987 | European Pat. Off. . |
| 0 383 676 B1 | 8/1990 | European Pat. Off. . |
| 3128 704 | 7/1981 | Germany . |
| 195 29 388 A1 | 1/1996 | Germany . |
| 608 368 | 5/1976 | Switzerland . |
| WO 87/05203 | 9/1987 | WIPO . |

OTHER PUBLICATIONS

International Search Report dated Nov. 24, 1997 relating to corresponding application PCT/US97/12909.

*Primary Examiner*—David Isabella
*Attorney, Agent, or Firm*—Terry L. Miller; Debra D. Condino; Guy L. Cumberbatch

[57] ABSTRACT

A prosthetic mechanical valve includes a base portion defining a through blood flow pathway closed by at least a pair of valve leaflets. The valve leaflets are pivotally carried by the base portion and movable in response to dynamic blood fluid pressures between a first position at which the leaflets close blood flow through the pathway and a second open position allowing blood flow in the pathway. A pair of confronting magnets are carried one to each of the pair of valve leaflets and attract one another. The magnetic forces of attraction between the pair of magnets imparts a biasing torque to the valve leaflets which tends to synchronize pivotal movements of the leaflets, cushions their sealing contact, quiets valve operation, and biases the leaflets toward a third partially open position. As a result, under conditions of nearly balanced blood fluid pressures across the pair of valve leaflet they anticipatorily open toward their third position to improve pumping effectiveness. Also, at about the end of a blood pumping stroke, the valve leaflets anticipatorily close from their fully open position toward the third position to reduce regurgitation flow and quiet the valve.

49 Claims, 7 Drawing Sheets

MECHANICAL PROSTHETIC VALVE, AND METHODS OF ITS CONSTRUCTION AND OPERATION

BACKGROUND OF THE INVENTION

1. Field of the Invention

The present invention is related to the field of prosthetic mechanical replacement valves for human implantation. More particularly, the present invention is directed to a mechanical heart valve which includes a base portion which is attachable to a patient's heart tissue in place of a natural heart valve. The valve includes a base portion which defines a through blood passageway. The blood passage way is occluded by a movable valve member assembly having at least a pair of valve leaflets movable between a first position and a second position. In the first position the valve leaflets cooperate with one another and with the base portion to close the blood passageway. The leaflets are pivotal to a second fully open position in which the leaflets swing away from sealing cooperation with one another into a position close to axial alignment with the passageway to open blood flow therethrough. The leaflets are interrelated with one another to yieldably bias the leaflets toward a partially open third pivotal position intermediate of the first and second positions.

2. Related Technology

A mechanical heart valve is known according to U.S. Pat. No. 4,276,658, issued 7 Jul. 1981 to St. Jude Medical, Inc., of St. Paul, Minn., and disclosing what is generally known as the "St. Jude valve". This mechanical heart valve includes a base portion defining a through blood passageway and pivotally carrying a pair of valve leaflets. The valve leaflets are sealingly cooperable with each other and with the base member to occlude the blood passageway. Alternatively, in response to dynamic blood fluid forces, the leaflets are pivotal to another position opening blood flow in one direction through the blood passageway. The dynamic blood fluid forces are able to pivot the leaflets between their open and closed positions to allow peristaltic pumping of blood by the patient's heart in which the valve is installed.

One recognized disadvantage of the St. Jude valve is that the leaflets do not open in anticipation of a pumping stroke of the heart, as do natural valves. That is, the natural valve will open slightly in response to a balance of fluid blood pressure on each side of the valve. This pressure-balanced anticipatory opening of the natural valves allows a better, more complete filling of the ventricle of the heart. The St. Jude valve which lacks this anticipatory pressure-balanced opening produces a relatively decreased blood pumping efficiency of the heart.

Another recognized disadvantage of the St. Jude heart valve is that the leaflets also do not begin to close in anticipation of the end of a pumping stroke of the heart. As a result, regurgitation blood flow must take place in order to begin and complete closing of the valve. Because the valve leaflets are fully open when this regurgitation flow takes place, the leaflets slam shut from a fully open position. The leaflets thus dynamically impact with one another and with the base member upon movement from their open position to their closed position in sealing cooperation with one another and the base member. A consequence of this impact upon valve closing is an undesirably high wear rate of the valve, and an undesirable impact noise. Generally, this undesirable impact noise can be heard externally of the patient as a clicking noise. While some patients perceive this clicking noise as comforting and indicating that their new prosthetic heart valve is working properly, other patients and some of those around them, view this operating click as undesirable and distracting.

It should be noted that conventional mechanical heart valves of the St. Jude type may demonstrate some asymmetrical and/or asynchronous movement of their valve leaflets in respect to one another. That is, the valve leaflets of a conventional mechanical heart valve may not always move in pivotal symmetry or in pivotal synchronization with one another. Also, the asymmetry or asynchronous motion contributes to an increased closing impact for the trailing one of the valve leaflets.

One solution to this wear, noise, and lack of anticipatory opening of the St. Jude-type valve is presented by U.S. Pat. No. 4,605,408, issued 12 Aug. 1986 to Alain Carpentier. According to the teaching of the '408 patent, the leaflets of a mechanical heart valve are biased toward an open position by either a leaf spring device effective while the leaflets are close to their seats, or by a pair of magnets repelling one another. One of the magnets of each pair of magnets is taught to be carried in a leaflet, while the other magnet of each pair is carried by the base member adjacent to the valve seat. The magnets are oriented to repel one another. As a consequence, the valve leaflets are urged away from their seats. The effective bias provides a closing cushion as the leaflets approach their seats, and also urges the leaflets off their seat to provide an anticipatory opening of the valve.

Unfortunately, the teaching of the '408 patent has never been possible to implement in a safe and effective mechanical heart valve. The embodiment having a leaf spring has not been accepted because of the possibility of breakage of the spring and of the broken spring becoming a foreign body movable in the circulatory system. The embodiment having opposed magnets carried by the leaflets and the base member has never been commercially implemented because of a variety of problems with this design. One problem is that the available physical space for locating the magnets in the edge portions of the leaflets (where they must be located to oppose magnets in the base portion) has been too constrained to receive effectively sized magnets. Another problem has to do with locating the magnets in an area of high contact stress, which accelerates fatigue problems with the structure of the valve.

Another proposed solution to the deficiencies of conventional prosthetic mechanical heart valves is presented by U.S. Pat. No. 5,123,918, issued 23 Jun. 1992 to Philippe Perrier, et al. According to the teaching of the '918 patent, a tri-leaflet prosthetic heart valve includes magnets in the leaflet corners which attract one another. This attraction of the leaflets for one another is contrary to anticipatory opening of the leaflets because the magnets attract one another and tend to latch the valve in a closed position. In the open position of the valve the magnets of the leaflets are confronted by like-poled magnets carried in aligned locations of the base portion of the valve. Consequently, these magnets repel one another to urge the leaflets toward a closed position. In other words, the valve leaflets are urged radially inwardly away from the base portion to provide anticipatory closing of the leaflets.

However, this anticipatory closing of the '918 patent is only the result of a bias from the fully open position of the valve toward a closed position. Due to the magnetic attraction of the valve leaflets for one another this valve is also magnetically urged to its closed position. In this design, there does not appear to be any bias of the valve leaflet from their closed position toward a dynamically-stable partially open position intermediate of the closed and fully open positions.

Still another mechanical prosthetic heart valve is known according to European Patent Office publication No.0023797A1. This publication is believed to disclose a mechanical prosthetic heart valve in which the valve leaflets both pivot and translate simultaneously at they move between their open and closed positions. This valve is not believed to provide either anticipatory opening or anticipatory closing of the valve leaflets. There does not appear to be any resilient bias of the valve leaflets toward a particular valve position.

In view of the above, it would be desirable to provide a mechanical heart valve which avoided one or more of the deficiencies of the conventional technology.

Particularly, it would be desirable to provide a mechanical heart valve which cushions the closing motion of the leaflets upon contact with each other and with the base member of the valve.

Additionally desirable features of such a mechanical heart valve would be realized if the valve were to have an anticipatory pressure-balanced opening function and a bias toward synchronous operation of the valve leaflets.

Still another feature of such a mechanical heart valve would be realized if the cushioning effect upon closing of the valve were effective to reduce the noise of operation of the valve.

An additional desirable feature would be to have the leaflets urged resiliently toward a position of anticipatory closing so that the leaflets are not slammed closed from their fully open positions by regurgitation flow.

Further to the above, a desirable feature for such a prosthetic heart valve would be for the valve leaflets to be biased both from their closed position and from their fully open position toward an intermediate partially open and dynamically stable position. This feature provides both anticipatory opening and anticipatory closing of the valve.

Another desirable feature would be for a prosthetic heart valve to have leaf lets which have symmetrical or at least synchronous pivotal motions between their open and closed positions.

SUMMARY OF THE INVENTION

In view of the above, it is an object for this invention to overcome one or more of the deficiencies of the conventional technology.

Another object for this invention is to provide a mechanical heart valve which cushions the closing motion of the leaflets.

Still another object for the present invention is to provide a mechanical heart valve having an anticipatory pressure-balanced opening function and a bias toward synchronous operation.

Yet another object for this invention is to provide a cushioning effect upon closing of the valve effective to reduce operating noise and wear of the valve.

Further, an object of this invention is to provide a prosthetic mechanical valve in which the leaflets are yieldably biased from their fully open position toward a partially open position, so that open position of the leaflets beyond this partially open position is a function of blood velocity through the valve.

Accordingly, the present invention provides a mechanical prosthetic valve for human implantation, the valve comprising a base portion defining a blood flow pathway therethrough; a pair of valve leaflets pivotally disposed in the blood flow pathway and responsive to blood fluid pressure to pivot between a first position of occluding cooperation both with one another and with the base portion to inhibit blood flow in the pathway, and a second fully open pivotal position opening blood flow in the pathway; and a mechanism for yieldably biasing the pair of valve leaflets both from the first position and from the second position toward a third pivotal position intermediate of the first and the second pivotal positions.

According to another aspect, the present invention provides a method of making a mechanical prosthetic heart valve, the method comprising steps of: providing a base portion defining a blood flow pathway therethrough; providing a pair of fluid pressure responsive valve leaflets; disposing the a pair of valve leaflets in the blood flow pathway and pivoting the pair of leaflets in response to blood fluid pressure between a first position of sealing cooperation both with one another and with the base portion to occlude blood flow in the pathway, and a fully open second position in which the leaflets open blood flow through the pathway; and yieldably biasing the pair of valve leaflets to a dynamically stable third pivotal position intermediate of the first and the second positions.

Another aspect of the present invention provides a method of operating a mechanical prosthetic valve in association with a heart which during a pumping stroke provides pulsatile blood flow, the valve including a base portion defining a blood flow pathway therethrough, a pair of fluid pressure responsive valve leaflets pivotally disposed in the blood flow pathway and pivoting in response to blood fluid pressure between a first position and a fully open second position, in the first position the pair of valve leaflets sealingly cooperating both with one another and with the base portion to occlude the blood flow pathway, and in the second pivotal position the pair of valve leaflets being pivoted out of sealing cooperation with one another and the base portion to open blood flow via the pathway; the method comprising steps of: yieldably biasing the pair of valve leaflets to a dynamically stable third pivotal position intermediate of the first and second positions; and using the yieldable bias to provide an anticipatory closing of the pair of valve leaflets from the second position toward the third position substantially at an end of the pumping stroke.

Still another aspect of the present invention provides a mechanical prosthetic heart valve including an annular base portion defining a blood flow pathway therethrough; a pair of masses formed of magnetic material; and at least a pair of valve leaflets pivotally disposed in the blood flow pathway and each pivoting about a respective pivot axis in response to blood fluid pressure between a first pivotal position of sealing cooperation with one another and the base portion to occlude blood flow in a first direction, and a second pivotal position in which the valve leaflets are spaced apart to open blood flow in an opposite second direction, each one of the pair of valve leaflets carrying a respective one of the pair of masses, at least one of the pair of masses having a magnetic pole thereof disposed to provide magnetic flux linking the pair of masses in mutually attracting relation, and each of the pair of masses being spaced from the respective pivot axis of the valve leaflet carrying each mass to swing in a respective arc as the valve leaflet pivots, the respective arcs being juxtaposed so that each valve leaflet of the pair magnetically affects and exerts a torque on the other to cooperatively bias the pair of valve leaflets to a dynamically stable third pivotal position intermediate of the first and second positions.

Additional objects and advantages of the present invention will be apparent from a reading of the following detailed description of two exemplary embodiments of the invention, taken in conjunction with the appended drawing Figures, in which the same reference numerals are used to indicate the same features, or features analogous in structure or function, throughout the drawings.

BRIEF DESCRIPTION OF THE DRAWING FIGURES

FIG. 11 provides a perspective view of a single valve leaflet as is used in the valve seen in FIGS. 8–10a;

DETAILED DESCRIPTION OF SEVERAL EXEMPLARY PREFERRED EMBODIMENTS OF THE INVENTION

Figure 1:
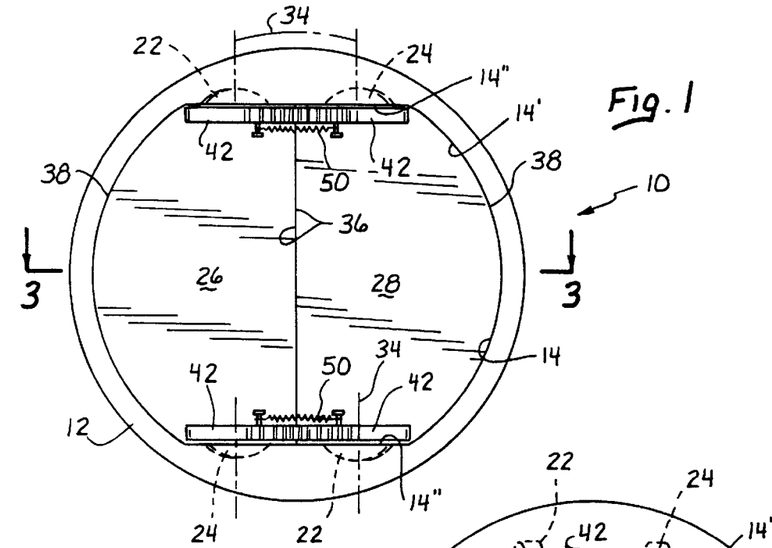
FIG. 1 provides a plan view of a mechanical heart valve embodying the present invention, and is viewed from the downstream side of the valve with an occluding valve assembly of the valve in a closed position.
Figure 2:
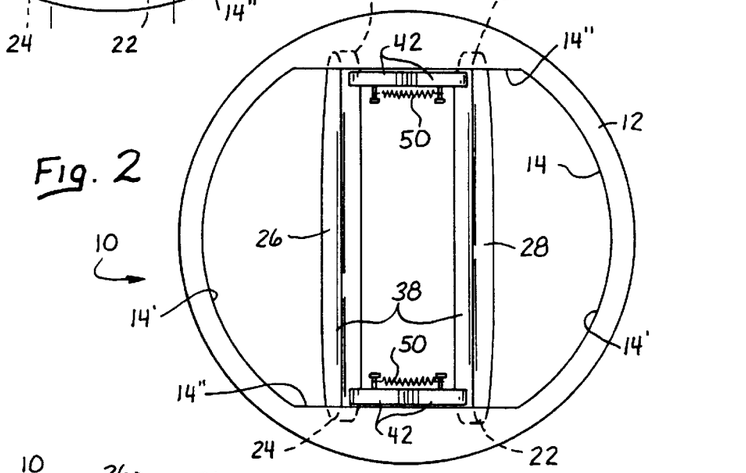
FIG. 2 is a plan view similar to FIG. 1, but with the occluding valve assembly of the valve in a fully open position.

Viewing FIGS. 1–4 in conjunction, and viewing first particularly FIG. 1, a mechanical heart valve 10 embodying the present invention is shown. Exemplary heart valve 10 includes a tubular base portion 12 defining a through blood flow pathway 14 for unidirectional flow of blood, as is indicated by arrow 16 seen in FIG. 3. The blood flow pathway 14 is generally cylindrical in plan view as is seen in FIGS. 1 and 2. This cylindrical blood flow pathway 14 includes a circular portion 14' and a pair of opposed axially extending surfaces 14".

Externally, in order to provide a way to allow a surgeon to secure the valve 10 to heart tissue the base portion defines an annular recess 18 between a pair of spaced apart radially outwardly extending flange features 20 and 20' at which a fabric suture ring (not shown) may be attached. As those ordinarily skilled in the pertinent arts will appreciate, this suture ring may be used by a surgeon to suture the valve 10 to heart or other patient tissues. Those ordinarily skilled will realize that a valve according to the present invention is equally applicable to mechanical hearts and heart assist devices, in which case base portion 12 may not be secured directly to heart tissue. Accordingly, the exterior configuration of the base portion 12 is illustrative only and is not to be taken as a limitation on the invention.

At each of the surfaces 14", the base portion 12 defines a pair of spaced apart butterfly-shaped recesses 22 and 24. Recesses 22 and 24 are semi-circular in cross section. Pivotally received at the pairs of recesses are a pair of respective valve leaflets 26 and 28, each of generally a D-shape. At opposite ends each valve leaflet 26 and 28 defines a respective one of a pair of opposite semicircular projections 30 and 32. One of the opposite projections 30, 32 of each leaflet 26 and 28 is pivotally received at each one of the recesses 22, 24 in order to pivotally receive and retain the pair of valve leaflets 26 and 28. The pivotal receipt of the projections 30 and 32 in recesses 22, 24 defines a respective pivot axis 34 for each individual one of the valve leaflets. Generally, the base portion 12 and valve leaflets 26 and 28 will be fabricated of non-magnetic material. For example, the base portion 12 may be made of pyrolytic carbon. The valve leaflets 26 and 28 may be made of titanium. Other materials may be used for both the base portion 12 and the valve leaflets 26, 28. However, in each case the materials of construction for the base portion and valve leaflets of the valve 10 are nonmagnetic.

As shown in FIG. 1, and as will be well understood by those ordinarily skilled in the pertinent arts, when leaflets 26, 28 are pivoted toward one another at their respective linear edges 36 to a first position, edges 36 sealingly cooperate with one another. Also, at their respective arcuate edges 38 opposite to the edge 36, each of the leaflets 26, 28 in its first position sealingly cooperates with inner cylindrical surface portion 14' defined by the base portion 12 as part of the blood flow pathway 14. Along the flat surface portions 14", the leaflets 26, 28 each define respective flat side edge portions 40 which are a sealingly close fit with the flat surfaces 14", and from which the projections 30, 32 extend. In the first position of the valve leaflets 26, 28 blood flow opposite to the direction of arrow 16 is occluded or substantially blocked.

Figure 3:
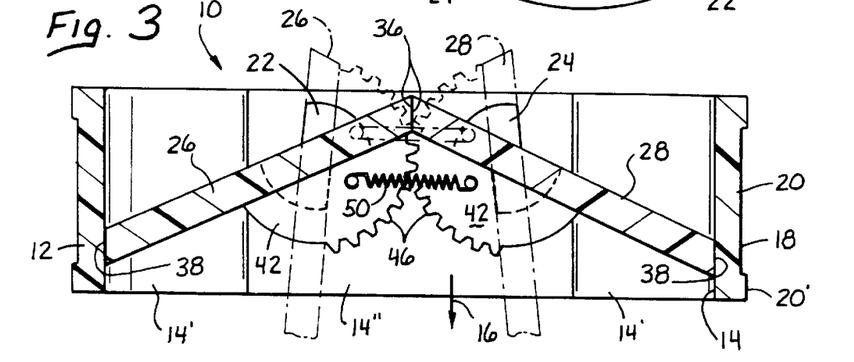
FIG. 3 is a cross sectional elevation view taken along line 3—3 of FIG. 1, but with the valve leaflets shown in a partially open (and also partially closed) neutral position, and with the fully open position of the valve leaflets as seen in FIG. 2 depicted in dashed lines.

However, as is directly illustrated in FIG. 2, and as is illustrated by dashed lines in FIG. 3, the valve leaflets 26, 28 are each movable to a second position of general alignment with the axis (i.e., parallel with arrow 16) of blood flow pathway 14. Understandably, the leaflets 26, 28 are movable between their first (closed) and second (fully open) positions in response to dynamic blood fluid pressures. It will be noted that the leaflets 26, 28 in this embodiment are not pivotally movable independently of one another, as will be explained. That is, the leaflets 26, 28 are engaged with one another for symmetrical and synchronous pivotal movement.

Figure 3A:
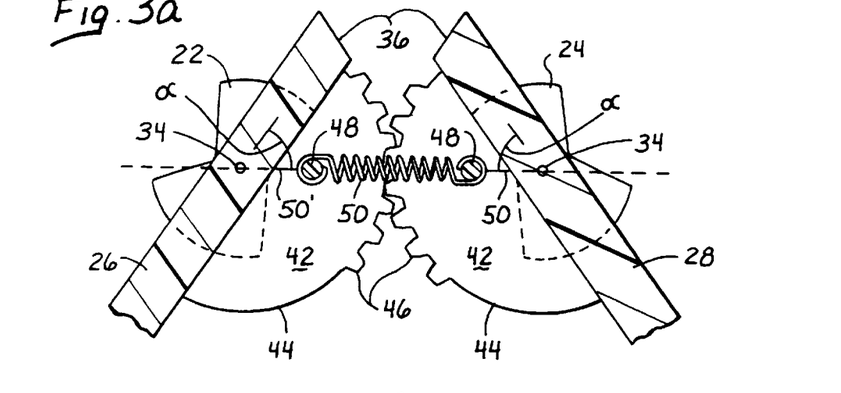
FIG. 3a is an enlarged fragmentary and somewhat diagrammatic cross sectional view of a portion of FIG. 3, and showing the valve leaflets of the valve in their neutral position.
Figure 4:
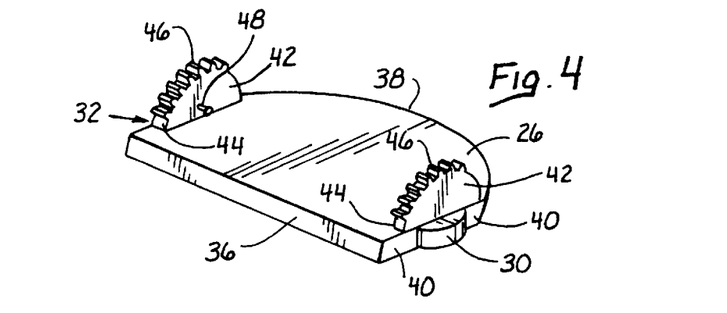
FIG. 4 provides a perspective view of a single valve leaflet as is used in the valve seen in FIGS. 1–3.

Further to the above, viewing FIGS. 3, 3a, and 4 in conjunction with one another, it is seen that each valve leaflet on its under side (i.e., the downstream side toward the viewer of FIGS. 1 and 2), includes a pair of spaced apart semicircular baffle portions 42. It will be seen that these baffle portions 42 are projections from each valve leaflet toward an adjacent leaflet, and provide a lever arm at which a torque can be exerted between the valve leaflets. These baffle portions each include a respective baffle edge surface 44 which confronts the similar baffle edge portion 42 and surface 44 of the other valve leaflet. Each baffle edge surface 44 is formed over at least a part of its circumference as a gear-tooth sector 46. The gear-tooth sectors 46 of the two valve leaflets 26, 28 drivingly engage one another at each baffle portion 42. As a result, the leaflets 26, 28 are geared together by the baffle portions 42 and gear tooth sectors 46 to pivot in symmetry and synchronization between their first and second positions as seen in FIGS. 1, 2, and 3 (dashed lines).

Still further to the above, it will be noted viewing FIG. 3a that in order to provide structure for connecting a biasing resilient element to the valve leaflets, each baffle portion 42 also includes a pin member 48 projecting toward the other opposite baffle portion 42 and generally parallel with the respective pivot axis 34 of the valve leaflet 26, 28. The pins 48 are spaced from the pivot axis 34 of the leaflet, and are angularly disposed relative to the plane of the leaflets at an angle indicated on FIG. 3a with the arrowed character a. As is seen in FIGS. 3 and 3a, the biasing resilient element connecting to the leaflets takes the form of a coil tension spring 50 extending between end portions of the opposed pins 48. The pins may be provided with heads (as shown), or with hooks or other configurations at their end portions to retain engagement of the spring 50. Alternatively, the spring 50 may be formed with off-set and hooked end portions at each end and may engage directly with the baffle portions, as by insertion and retention in respective holes drilled across the baffle portions. Many acceptable alternative ways of connecting a spring or other resilient member to the leaflets will suggest themselves to those ordinarily skilled in the pertinent arts.

It will be recalled that the leaflets 26, 28 are pivotal in the base portion 12, as was described above. Consequently, because the pins 48 are angularly positioned relative to the first (closed) position and second (fully open) position of the valve leaflets 26, 28 (recalling the angle α noted above) the tension force from the springs 50 (indicated by arrows 50' on FIG. 3a) pivotally biases the leaflets to a third position intermediate of the first and second positions, as is indicated in FIG. 3a. This third pivotal position is a dynamically stable, or "neutral" position for the valve leaflets 26, 28. In other words, in this neutral position, the pins 48 are disposed generally on a line extending between the pivot axes 34. The valve leaflets 26, 28 are yieldably biased toward this dynamically stable intermediate neutral position as is depicted in FIG. 3a by the dashed line passing through these points. Also importantly, it will be noted that the pins and baffle portion of each leaflet provides an effective lever arm upon which the spring force from spring 50 may exert a torque on each of the leaflets to pivot them toward this neutral position. By "dynamically stable," is meant both that pivotal perturbations of the valve leaflets from this position are resisted by the effective resilient bias (i.e., the bias mechanism yields to allow forces of sufficient magnitude to both close and fully open the valve), and that the bias tends to return the valve leaflets to this neutral position after a perturbation.

As can be easily appreciated, when the valve leaflets 26, 28 are in their fully closed position, the force from springs 50 tends to open the leaflets toward the illustrated third (i.e., neutral) position. Consequently, an anticipatory pressure-balanced opening of the leaflets is provided which improves the pumping effectiveness of the heart. That is, when the blood pressure across the closed valve leaflets becomes substantially equal, the leaflets will pivot from their closed positions to the third position. Actually, as those ordinarily skilled in the pertinent arts will recognize, the closed valve leaflets will begin this anticipatory opening before the pressure differential across the leaflet actually reaches zero. This is because as the pressure differential across the closed leaflet decreases and approaches zero, a time will be reached when the effective torque on the leaflets from the pressure differential is just balanced by the effective opening torque on the leaflets from the springs 50. Beyond this time, as the pressure differential across the leaflets decreases further the leaflets will begin their anticipatory opening pivotal movement.

Further, when the leaflets are in their fully open position, the springs 50 provide a bias tending to move the leaflets from this fully open position toward the third position. Consequently, the position of the leaflets between the fully open position and the third position becomes a function of the balance between blood flow forces (i.e., blood flow velocity) and the spring bias on the leaflets. Accordingly, as blood flow velocity slows toward the end of a contraction stroke for the heart, the leaflets 26, 28 move from the fully open position toward the third position. Later, when blood regurgitation flow begins, the leaflets are closer to their closed position and close quicker while moving through a smaller angle and acquiring a lesser energy from the regurgitation blood flow. In this way, the energy acquired by the leaflets upon closing is decreased compared to conventional valves, and the wear and noise of the valve is decreased.

Because the leaflet are closer in their third position to the closed position than they would be had they remained fully open, they have a shorter distance to move to effect closing of the valve, and a smaller blood regurgitation flow is allowed. This improves pumping efficiency of the heart. Still further, as the valve leaflets move from their fully open position through the third position, and toward the closed position, the spring bias becomes one tending to open the leaflets. Blood regurgitation flow pressure insures that the leaflets 26, 28 do close. But, the opposing spring bias takes energy away from the closing leaflets to cushion their closing and further quiet the valve 10.

Figure 5:
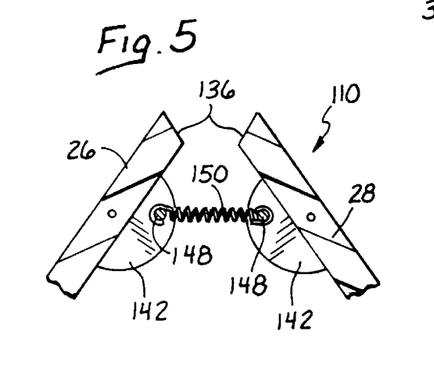
FIG. 5 is an enlarged and somewhat diagrammatic cross sectional view similar to FIG. 3a, but showing a second alternative embodiment of the invention.
Figure 6:
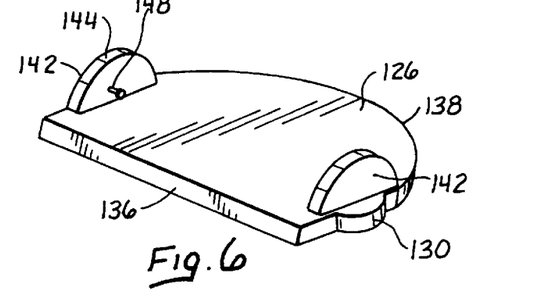
FIG. 6 provides a perspective view of a single valve leaflet as is used in the valve seen in FIG. 5.

FIGS. 5 and 6 illustrate an alternative embodiment of the inventive valve in which synchronous movement, but not necessarily symmetrical movement, of the valve leaflets is assured. In order to obtain reference numerals for use in describing this alternative embodiment of the invention, features which are the same as or analogous in structure or function to those of FIGS. 1–4 are referenced in FIGS. 5 and 6 using the same numeral used above, and increased by one-hundred (100).

Viewing FIGS. 5 and 6 in conjunction with one another, it is seen that each valve leaflet on its under side also includes a pair of spaced apart semicircular baffle portions 142. These baffle portions 142 are each projections from a leaflet toward a next-adjacent leaflet, and each includes a respective baffle edge surface 144 which confronts the similar baffle edge portion surface of the adjacent valve leaflet. However, each baffle edge surface 144 is smooth and semi-circular to confront but not touch the opposing baffle edge surface 144. In other words, there in no driving engagement of one valve leaflet with the other in a positive driving sense like there was with the first embodiment depicted and described above.

It will be noted, however, that each baffle portion 142 does include a pin member 148 projecting toward the other opposite baffle portion 142 and generally parallel with the respective pivot axis 134 of the valve leaflet 26, 28 just as in the first embodiment. Also similarly to the first embodiment, a coil tension spring 150 extends between the opposed pins 148. The pins 148 are angularly positioned relative to the first (closed) position and second (fully open) position of the valve leaflets 126, 128, so that the tension force from the springs 150 bias the leaflets to a neutral third position intermediate of the first and second positions.

Accordingly, the leaflets 126, 128 are resiliently biased toward synchronous movement between their first and second position, but are not positively driven in symmetrical pivotal motion, as were the leaflets of the first embodiment. Viewing FIG. 7, a spring force diagram is provided which helps explain this resilient bias toward synchronous pivotal motion of the leaflets 126 and 128. In the illustrated position of the leaflets, suppose that unbalanced blood flow fluid forces (illustrated by arrows 116, the differing lengths of which indicate differing flow velocities) are causing the right-hand leaflet to be open slightly more than the left-hand leaflet.

Figure 7:
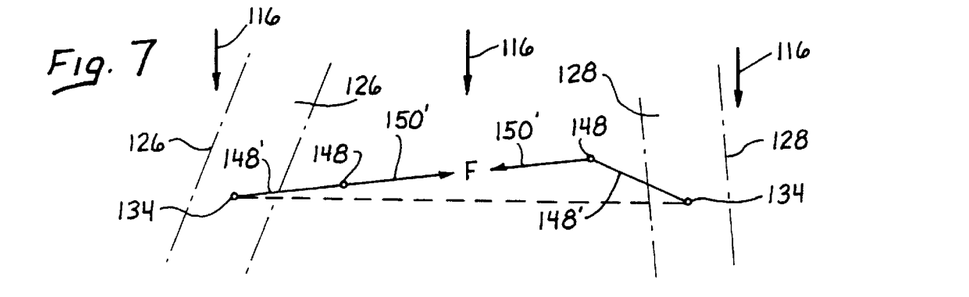
FIG. 7 is a force vector diagram illustrating an aspect of operation of the alternative embodiment of the invention seen in FIGS. 5 and 6.
Figure 8:
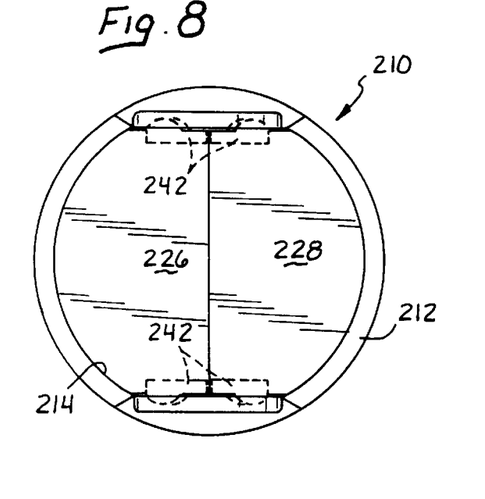
FIG. 8 provides a plan view of a third alternative embodiment of a mechanical heart valve embodying the present invention, and is viewed from the upstream side of the valve with an occluding valve assembly of the valve in a closed position.
Figure 9:
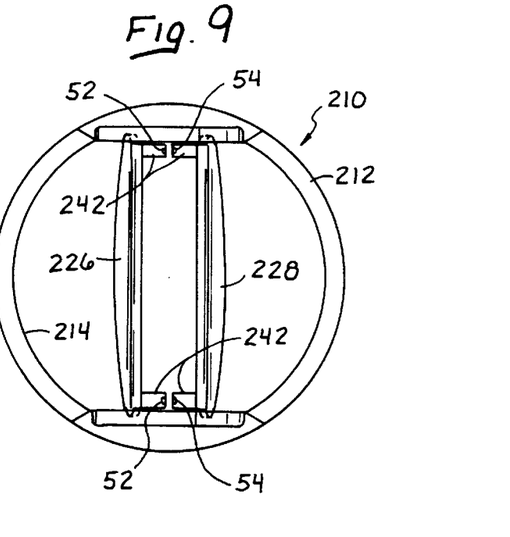
FIG. 9 is a plan view similar to FIG. 8, but with the occluding valve assembly of the valve in a fully open position.

As a result, the pins 148 will have the positions indicated, and the spring forces (indicated by force arrows 150') will extend between the pins 148. It is easily seen that the spring forces will tend to pivot the left-hand leaflet so that the spring forces are aligned with the line 148' between pin 148 and the pivot axis 134 for the left-hand leaflet 126. In other words, the spring forces 150' will tend to bring the pins 148 as close together as possible, which results in both of the pins 148 and one of the pivot axes 134 tending to be aligned along a straight line. It is easily understood that in the absence of unbalanced torques on the leaflets, the pins 148 will be aligned along a line parallel with one connecting the pivot axes 134.

As can be easily appreciated, when the valve leaflets 126, 128 are in their fully closed position, the force from springs 150 tends to open the leaflets toward the illustrated third position. Consequently, an anticipatory opening of the leaflets is provided which improves the pumping effectiveness of the heart. Further, when the leaflets are in their fully open position, the springs 150 provide a bias tending to move the leaflets from this fully open position toward the third position. Consequently, in this second embodiment as well, the position of the leaflets between the fully open position and the third position becomes a function of the balance between blood flow forces (i.e., blood flow velocity) and the spring bias on the leaflets. Accordingly, as blood flow velocity slows toward the end of a contraction stroke for the heart, the leaflets 126, 128 move from the fully open position toward the third position.

FIGS. 8, 9, 10, 10a, and 11 illustrate a third alternative embodiment of the inventive valve in which synchronous movement, but not necessarily symmetrical movement, of the valve leaflets is provided. In order to obtain reference numerals for use in describing this alternative embodiment of the invention, features which are the same as or analogous in structure or function to those of FIGS. 1–7 are referenced in FIGS. 8–11 using the same numeral used above, and increased by two-hundred (200).

Viewing FIGS. 8–11 in conjunction with one another, it is seen that each valve leaflet 226, 228 on its under side includes a pair of spaced apart semicircular baffle portions 242. These baffle portions each include a respective baffle edge surface 244 which confronts the similar baffle edge portion surface of the other valve leaflet. However, each baffle edge surface 244 is smooth and semi-circular to confront but not touch the opposing baffle edge surface 244. Again, in this embodiment there is no driving engagement of one valve leaflet with the other in a positive driving sense like there was with the first embodiment depicted and described above. This embodiment does not even include pins 148 and springs 150 like the second embodiment described above. Instead, the resilient bias toward the neutral position of the valve leaflets 226, 228 is provided by a pair of permanent magnets 52, 54 inset into the surfaces 244 of the baffle portions 242. Preferably, the permanent magnets 52, 54 are formed of samarium cobalt magnetic material, and are covered over by a closure portion (not shown) of the leaflet 226, 228 to prevent contact of the patient's blood with the magnetic material.

Figure 12:
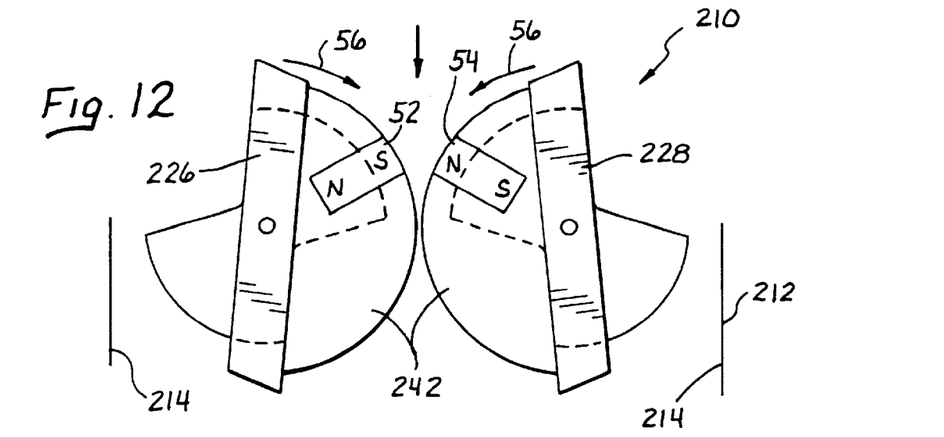
FIGS. 12–14 are similar enlarged diagrammatic cross sectional elevation views of the embodiment seen in FIGS. 8–11, and illustrating the valve leaflets in different operating positions.
Figure 13:
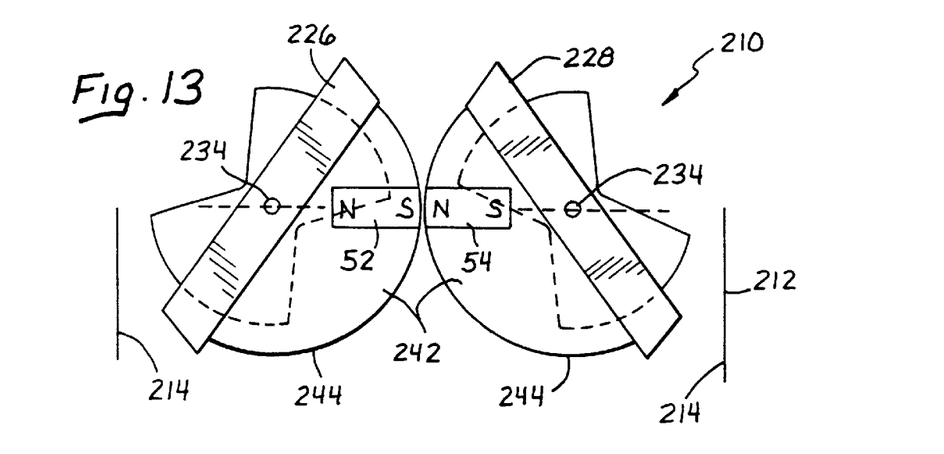
Figure 14:
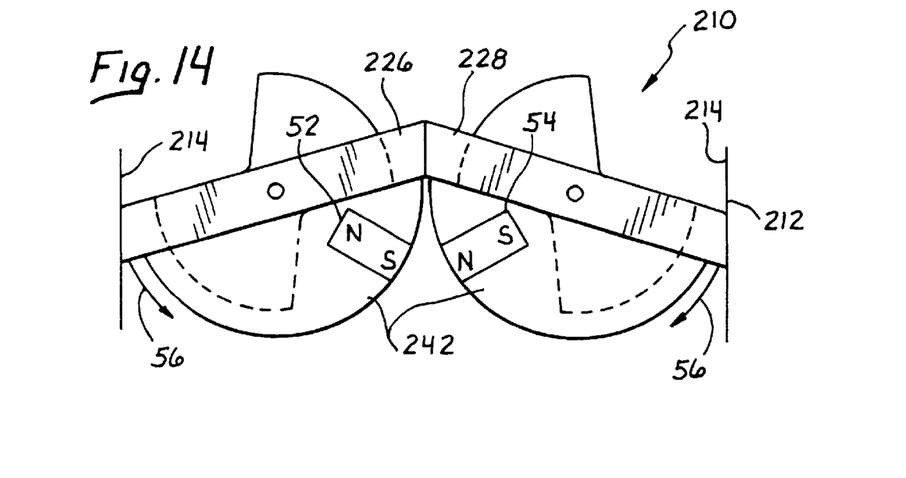

The permanent magnets 52 and 54 are oriented with opposite magnetic poles confronting and attracting one another (as is indicated in FIGS. 12–14 by the "N", and "S" characters, indicating the north and south magnetic poles of the permanent magnets 52 and 54. Viewing FIGS. 12–14, it is seen that in the fully open (i.e., second) position of the valve as is seen in FIG. 12, the magnets 52 and 54 provide a biasing torque (indicated by arrows 56) toward the neutral position (i.e., the position seen in FIG. 13). Also as seen in FIG. 14, when the valve leaflets are in the fully closed position, the biasing torque 56 is again toward the neutral position. In the neutral position of the valve leaflets seen in FIG. 13, the magnetic poles of the magnets 52, 54 are aligned along a line connecting the pivot axes 234. In this instance, the magnetic poles of the magnets 52, 54 are aligned radially with respect to the pivot axis 234 of the respective valve leaflets, and the radial spacing of the attracting opposite poles (i.e., those poles close to the surface 244) of the magnets provides the necessary lever arm so that the magnetic attraction force can exert a torque on the leaflets.

Figure 10:
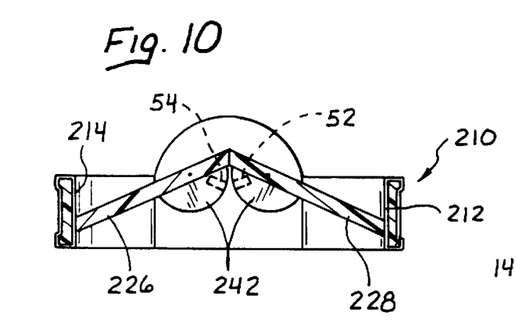
FIG. 10 is a cross sectional elevation view taken along line 10—10 of FIG. 8, with an open position of the valve leaflets as seen in FIG. 9 depicted in dashed lines.
Figure 10A:
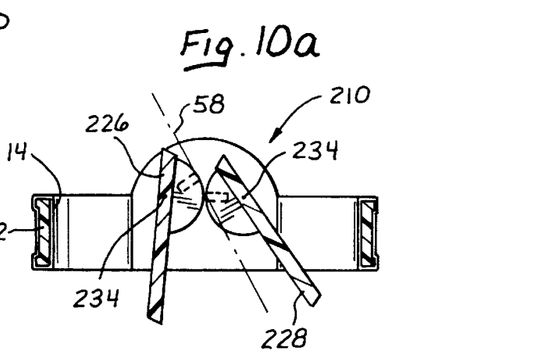
FIG. 10a is a fragmentary cross section view similar to FIG. 10, but showing the valve leaflets of the valve in asynchronous movement.
Figure 11:
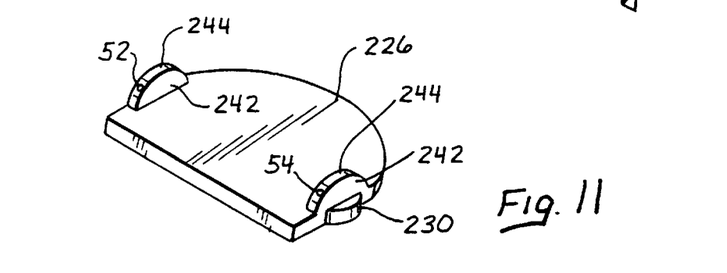

Further to the above, it is seen that the magnetic attraction force between magnets 52, 54 acts just like the spring force from spring 150 of the second embodiment described above. Further, FIG. 10a provides a diagrammatic view similar to FIG. 7 showing how the magnetic forces tend to urge the leaflets toward synchronous pivotal movement That is, as depicted in FIG. 10a, if the leaflets are experiencing non-synchronous pivotal motion, then the biasing magnetic attraction between the leaflets will tend to slow the "leading" leaflet and accelerate the "lagging" leaflet. Viewing FIG. 10a, if the right-hand leaflet is leading the left-hand leaflet in moving toward the first position (i.e., is closer to its closed position), then magnets 52 and 54 do not align with one another along or parallel with a line passing through the leaflet pivot centers 234 (i.e., the leaflets do not have the pivotal relationship of symmetry illustrated in FIGS. 10, and 12–14).

Instead of symmetry and alignment along a line connecting the pivot axes 234, the confronting and attracting poles of magnets 52 and 54 align along a skewed action line 58. Action line 58 passes below the pivot axis 234 for the right hand leaflet 228 (representing a clockwise torque on this leaflet) and above the pivot axis 234 for the left-hand leaflet 226 (also representing clockwise torque on the left-hand leaflet). Effectively, the applied magnetic torques tend to slow down the pivotal movement of the leading leaflet and to speed up the pivotal movement of the lagging leaflet so that the leaflets are magnetically biased toward synchronous pivotal movements (not necessarily symmetrical movement because the leaflets may have differing angular velocities during various parts of the pivotal movement) between their open and closed positions. The same analysis applies when the leaflets are moving from their closed position toward their open position.

Still further to the above, it will be apparent that a magnet need not be used at both of the locations of the magnets 52 and 54 as described above. All that is required is that one be a magnet and the other be magnetic. The permanent magnet will still attract the magnetic material of the other member (i.e., 52 or 54), and the valve will operate as described above. Hereinafter, the numeral 52 is used to refer to the permanent magnet, and the numeral 54 is used to refer to the magnetic material which may be either a permanent magnet or simply magnetic. This aspect of the present invention presents a significant safety factor for embodiments constructed with two attracting permanent magnets. In the event that one of the magnets 52 or 54 loses part or all of its strength as a magnet, it will still remain as a mass of magnetic material which is attracted to the other permanent magnet of the pair. Consequently, the valve will continue to operate satisfactorily and to provide the advantages of the invention.

Figure 15:
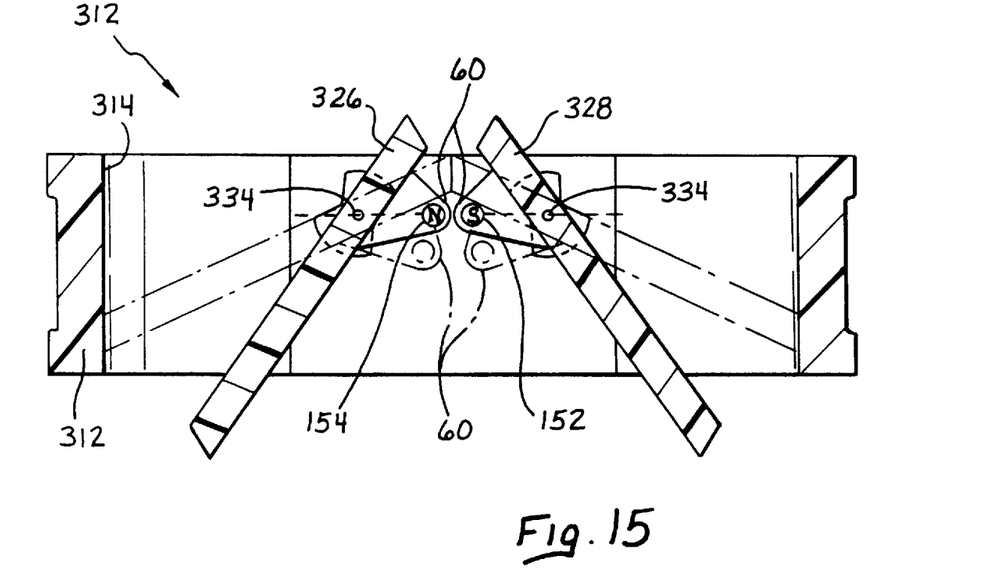
FIG. 15 is an enlarged partially cross sectional elevation view of a fourth alternative embodiment of a mechanical prosthetic valve.
Figure 16:
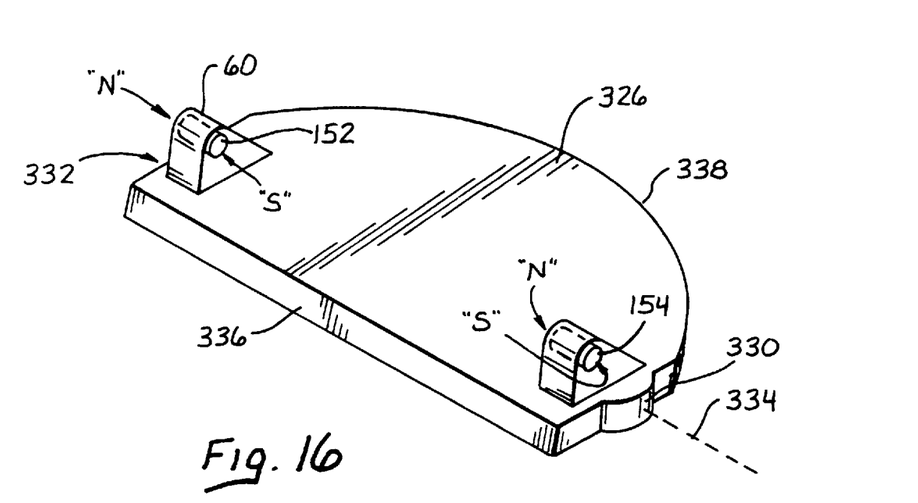
FIG. 16 provides a perspective view of a single valve leaflet as used in the embodiment of FIG. 15.

Further, FIGS. 15 and 16 illustrate a fourth alternative embodiment of the invention in which the same features or features analogous in structure or function are referenced with the same numeral used above and increased by three-hundred (300). Viewing FIGS. 15 and 16, it is seen that in this embodiment, the valve leaflets 326 and 328 each include a pair of spaced apart elongate bosses 60 extending generally parallel with the pivot axis 334 of the leaflets. Again, these bosses are seen as projections from each valve leaflet toward the other, and are seen to provide a lever arm so that a torque can be exerted on the respective leaflets. Each boss 60 carries a bar-like permanent magnet 152, 154 (or one magnet 152 while the other carries a mass 154 of magnetic material—recalling the explanation above). In this case, the magnetic materials 152, 154 are generally aligned with and spaced from the pivot axis 334 rather than in confronting relation with one another, as was the case with the embodiments described above. In other words, the magnets have their magnetic poles (indicated with the "N", and "S" characters on FIGS. 15 and 16) aligned generally parallel with the pivot axis 334. As can readily be seen, if two substantially identical valve leaflets having magnetic pole orientations as depicted are placed in cooperative position with one another as shown in FIG. 15, then the magnetically-opposite poles of the magnets 152, 154 will be magnetically coupled. In the event that a magnetic mass (i.e., rather than a magnet) is used at 154, then its position as a bar-like body is important (rather than its magnetic pole orientation), as will be readily apparent to those ordinarily skilled in the pertinent arts.

Further to the above, as is illustrated in FIG. 15, the spacing of the magnetic materials 152, 154 from the pivot axes 334 provides a lever arm, and these lever arms are angularly disposed relative to the valve leaflets 326, 328. Accordingly, the magnetic flux from at least one of the magnetic masses 152, 154 will couple between the two leaflets (depicted by dashed lines 60' on FIG. 15). In the neutral position for the leaflets, this coupling flux extends along a line extending between the pivot axes 334. As before, the magnetic coupling of the leaflets is effective in the first and second positions of the leaflets 326 and 328 to yieldably bias these leaflets toward the neutral position, as is depicted in FIG. 15.

FIGS. 17–20 depict a fifth alternative embodiment of the present invention in which the valve is configured similarly to that of the EP '797 publication discussed above in order to provide the leaflets with both a pivotal and a translational motion between their closed and fully open positions. Again, in order to obtain reference numerals for use in describing this embodiment of the invention, features which are the same as or analogous in structure or function to features depicted and described above are referenced with the same numeral used above and increased by four-hundred (400).

Viewing FIGS. 17–20 in conjunction, it is seen that the valve 410 includes a base ring portion 412, which in this case defines recesses 422 and 424 which are oval and diverging from one another in the downstream direction of blood flow through the valve. Also, in this case the projections 430 and 432 on the valve leaflets 426, 428 are semi-spherical in shape to be slidably and pivotally received in the recesses 422 and 424. Each leaflet 426 and 428 defines a pair of spaced apart baffle portions 442 which are partly semi-circular. Within each of the baffle portions 442 is carried one of a pair of attracting permanent magnets 452, 454 (or one permanent magnet 452 and a mass of magnetic material in cooperative opposition to the permanent magnet—the latter also being indicated by the numeral 454).

Figure 17:
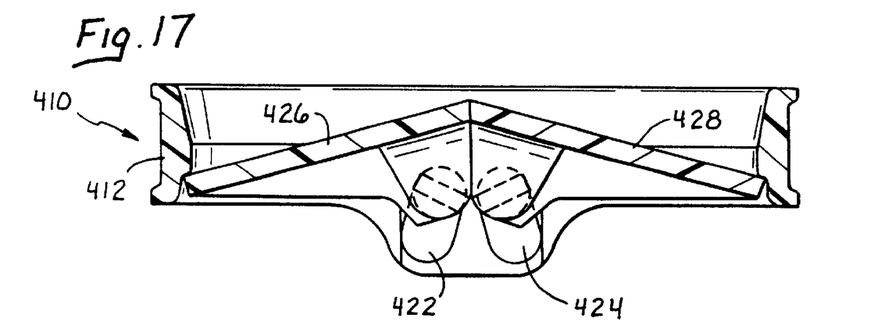
FIG. 17 provides a partially cross sectional elevation view of a fifth alternative embodiment of a mechanical prosthetic valve embodying the present invention, and is shown with an occluding valve assembly in the closed position.
Figure 18:
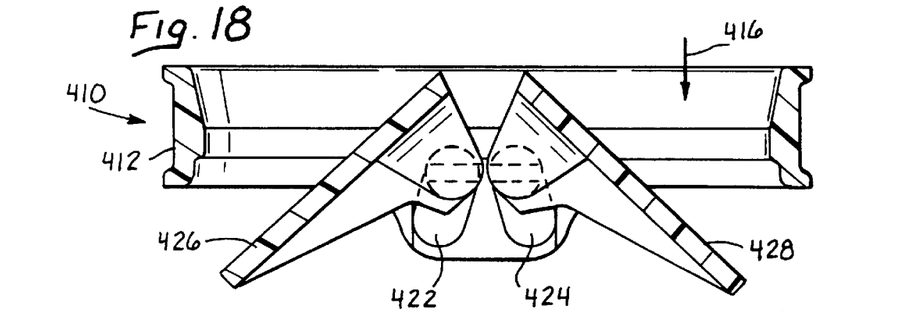
FIG. 18 provides a partially cross sectional elevation view of the fifth alternative embodiment of the mechanical prosthetic valve seen in FIG. 17, and is shown with an occluding valve assembly in a neutral position.
Figure 19:
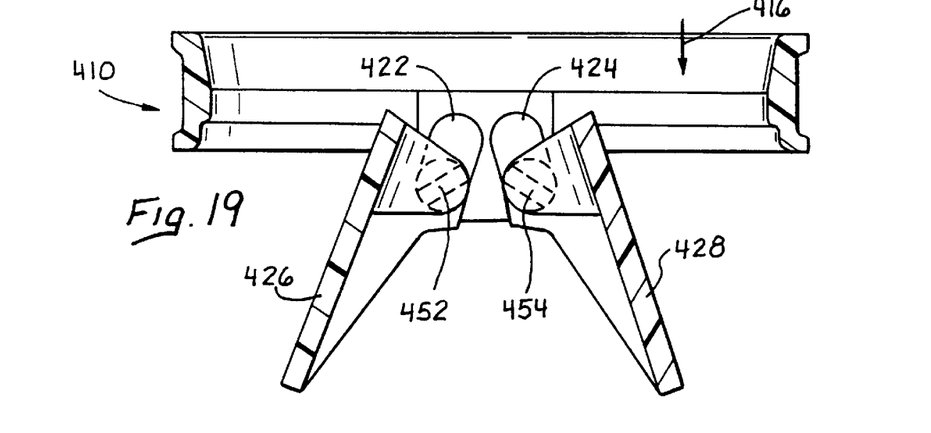
FIG. 19 provides a partially cross sectional elevation view of the fifth alternative embodiment of the mechanical prosthetic valve seen in FIGS. 17 and 18, but is shown with the occluding valve assembly in a fully open position.
Figure 20:
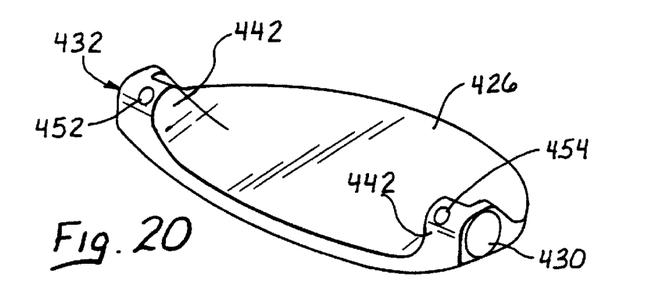
FIG. 20 provides a perspective view of a single valve leaflet as used in the embodiment of FIGS. 17–19.

In this case also, the magnetic coupling between the pair of leaflets allows each to exert a torque on the other, and yieldably biases the leaflets to a neutral position pivotally intermediate of the closed and fully open positions of the valve leaflets, as is indicated in FIG. 18. Those ordinarily skilled in the pertinent arts will realize that the leaflets 426, 428 translate and pivot simultaneously between their closed and fully open positions as seen in FIGS. 17 and 19. Because of the magnetic bias coupling provided between the valve leaflets by the present invention, the leaflets tend to not only pivot in synchronization, but also to translate in synchronization. In view of the description above, further description and explanation of the embodiment depicted in FIGS. 17–20 should be unnecessary for those ordinarily skilled in the pertinent arts.

It will also be apparent that prosthetic heart valve designs can have the hinge features reversed (i.e., with a recess on the valve leaflets and projections on the base portion which are received into the recesses of the leaflets) with the hinge design having virtually no effect on the function of the inventive features.

Figure 21:
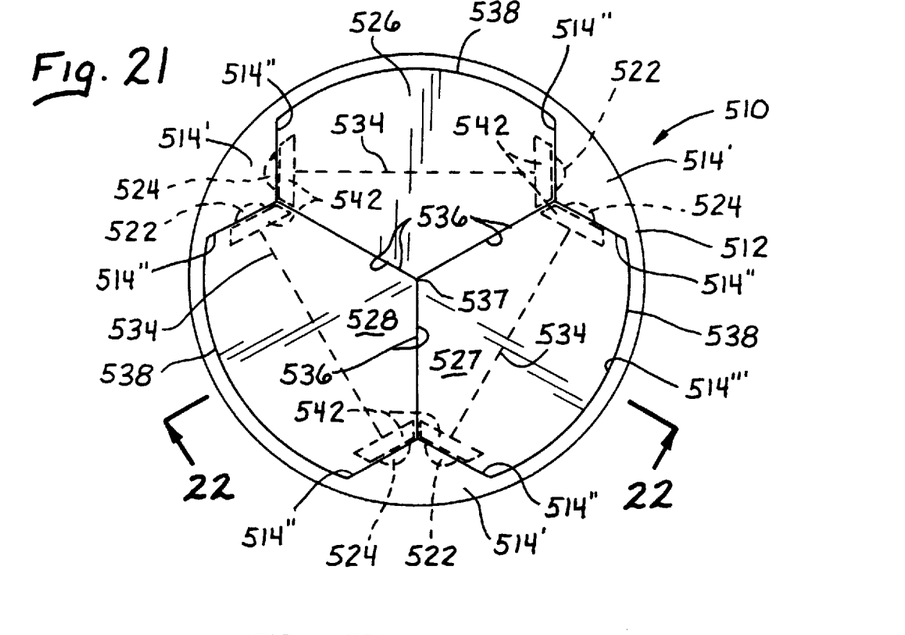
FIG. 21 is a plan view similar to FIG. 1 illustrating a sixth alternative embodiment of a mechanical prosthetic valve embodying the present invention.
Figure 22:
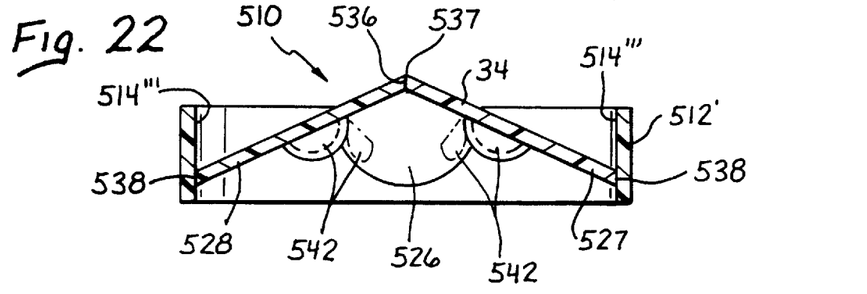
FIG. 22 provides a fragmentary elevation view similar to that of FIG. 3, but showing the embodiment of FIG. 21 taken along the section line indicated in FIG. 21 with the arrows 22—22.
Figure 23:
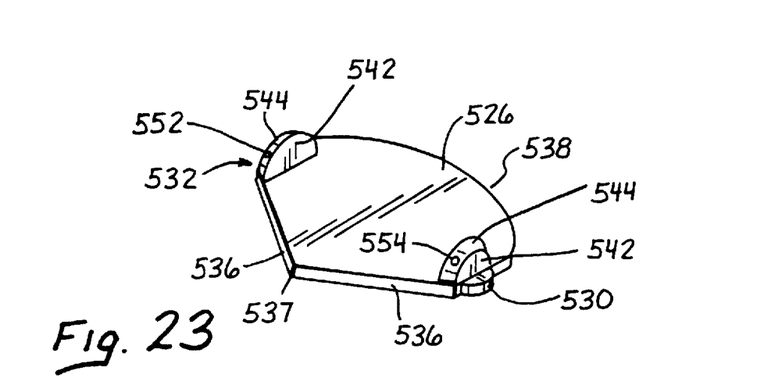
FIG. 23 provides a perspective view of a single valve leaflet as used in the embodiment of FIGS. 21 and 22.

Viewing FIGS. 21–23, a sixth alternative embodiment of a mechanical heart valve 510 embodying the present invention is shown. In accord with the precedent established above, the reference numerals for this embodiment are increased by five-hundred (500). The valve 510 includes a tubular base portion 512 with a cylindrical through blood flow pathway 514. The base portion 512 also defines three projections 514' each of which is generally triangular in plan view and defines a pair of angularly disposed axially extending flat side surfaces 514". The surfaces 514" are angularly spaced apart from one another by approximately 120 degrees in plan view, and are parallel in opposed pairs. In confronting relation, the spaced apart surfaces of confronting surface portions 514" each define one of a pair of spaced apart wing-shaped recesses 522 and 524.

However, in this embodiment of the present invention, recesses 524 and 526 are on relatively angularly disposed surfaces of the respective ear portions 514. Recesses 522 and 524 pivotally receive and retain a respective one of a pair of opposite semi-circular projections 530 and 532 disposed at opposite ends of each of the three generally arrowhead-shaped valve leaflets 526, 527, and 528. In this tri-leaflet embodiment, the sealing surface 536 at which the leaflets sealingly cooperate with one another is chevron-shaped rather than straight as in the bi-leaflet designs.

The three valve leaflets 526, 527, and 528 are pivotally received in the blood flow pathway 514 in order to open and close in response to blood flow fluid dynamic pressures in association with a beating heart. When leaflets 526, 527, and 528 are pivoted toward one another at angularly disposed side edges 536 to a first position, these edges 536 sealingly cooperate with one another. Similarly to the bi-leaflet designs, at an arcuate edge 538 which is opposite to a point 537 defined by the intersection of chevron-shaped edges 536, each of the leaflets 526, 527, and 528 sealingly cooperates with a respective part of a generally circular (in plan view) inner cylindrical surface 514''' defined by the base portion 512' as part of the blood flow pathway 14. The valve leaflets 526, 527, and 528 are each movable to a second position of general alignment with the blood flow in flow pathway 514, as will be readily understood in view of the previous description of the bi-leaflet designs.

Valve leaflets 526, 527, and 528 each include a pair of spaced apart confronting semi-circular baffle portions 542. As shown in FIG. 22, the baffle portions 542 confront and closely approach one another at angularly disposed baffle edge surfaces 544, but do not touch one another. A pair of magnets 552 and 554 are inset into each confronting pair of baffles 542 at the surface 544. These magnet pairs yieldably bias the leaflets 526, 527, and 528 to a neutral position intermediate of the open and closed positions.

Accordingly, the three-leaflet exemplary embodiment of the invention seen in FIGS. 21–23 enjoys the same advantages as the two-leaflet exemplary embodiments of FIGS. 1–20. However, this valve design has a greater need of synchronization in the pivotal movements of the valve leaflets between their open and closed positions than does the two-leaflet designs. This is so because the three leaflets have a greater leaflet-to-leaflet sealing length at which the leaflets sealingly cooperate with one another, and cooperation of all three leaflets to define this sealing length is necessary in order to control leakage flow through the closed valve. In the event that one of the leaflets is lagging the others as the leaflets move to their closed position, the two leaflets which close first can effectively block the third leaflet from closing properly. Accordingly, leakage flow of this valve design can be a serious problem in the event of leaflet movements which are sufficiently non-synchronized.

Moreover, this three-leaflet embodiment of the inventive valve has three comparatively smaller leaflets which are individually of lesser mass than the leaflets of a bi-leaflet design. As a result, the leaflets are more responsive to the blood fluid dynamic forces. Additionally, the less massive leaflets of this three-leaflet embodiment acquire less energy during closing and impact one another and the base portion 512 with less energy and less noise. The three-leaflet embodiment also centralizes blood fluid flow through the valve in its open position much like a normal tri-cuspid heart valve.

In each of the alternative embodiments illustrated and described above, the preferred angular position for the neutral position of the valve is half way between the open and closed positions of the valve. This half-way location for the neutral position of the valve provides the best symmetry for the leaflets in response to the resiliently bias toward synchronous movements between the fully open and closed positions (recalling the diagram of FIG. 7). However, it will be understood that the neutral position for the valve leaflets may be selected as desired to influence operation of the valve.

Studies of the operation of valves embodying the present invention have shown that mitigation of closing energy and impact (and therefore of valve noise) by providing an anticipatory closing of the valve from its fully open position toward the neutral position is a salient feature of this invention. This feature quiets the valve's operation, reduces wear, reduces regurgitation blood flow, and improves pumping efficiency of the patient's heart. The present invention provides these advantages without using some expedient to simply bias the valve leaflets away from the base portion of the valve or constantly toward one another (which tends to latch the valve closed). Instead the present invention biases the valve leaflets yieldably toward a dynamically stable intermediate (i.e., neutral) position which is between the closed and fully open positions for the valve. This provides an anticipatory opening of the valve which further improves pumping efficiency, and cushions closing of the leaflets as they move in the closing direction against the bias, further reducing noise and wear. The interconnection of the valve leaflets improves synchronistic operation for the valve, and improves blood flow.

In view of the above, it is seen that the present invention provides all of:

a) a resilient bias of the valve leaflets toward synchronous pivotal movement between their open and closed positions;

b) cushioning of the closing movement of the valve leaflets upon contact with one another and the base member of the valve;

c) quieter operation of the valve and reduced wear;

d) anticipatory self-opening of the closed valve preparatory to a condition of balanced fluid pressures across the leaflets;

e) anticipatory closing of the valve from its fully open position toward the neutral position to assist in early full closing of the valve and reduced regurgitation of blood through the valve;

f) a valve leaflet position in the open positions (i.e., from fully open to the third position) which is a function of the balance between blood flow velocity forces and the resilient bias applied to the leaflets so that toward the end of a pumping stroke when the blood flow velocity slows the valve leaflets close toward the neutral position and have a shorter distance to move in order to fully close. This full closing movement is driven by regurgitation blood flow, but moves the leaflets through a smaller distance so that the leaflets acquire less energy in this closing movement; and g) in the embodiment of FIGS. 1–4, a truly symmetrical pivotal movement of the drivingly engaged valve leaflets between their fully open and closed positions.

While the present invention has been depicted and described by reference to several exemplary embodiments thereof, such reference does not imply a limitation on the invention, and no such limitation is to be inferred. Various modifications and alterations of the implementation of the present invention will suggest themselves to those ordinarily skilled in the pertinent arts. For example, it will be apparent that in the embodiments using magnetic material to yieldably bias the valve leaflets to the third (i.e., neutral) position, the masses of magnetic material do not necessarily have to be carried in a boss of baffle on the leaflet. The masses of magnetic material need only be arranged so that the magnetic force between the masses can exert a torque on the valve leaflets urging them toward the third position. This arrangement could include, for example, a simple projection from each of the leaflets toward each other and having the associated magnetic mass disposed in this projection. At least one of the masses will be a permanent magnet in order to provide a magnetic flux. However, the other magnetic mass could simply be a body of soft iron or other magnetic material. Another possible modification is to use a pair of magnetic masses which are bar-like in physical configuration. At least one of the masses would be a magnet, and would have magnetic poles at its opposite ends By simply drilling an angulated hole through each leaflet to accept one of the bar-like masses in confronting position with the magnetic mass of the other leaflet the magnetic masses may be placed in cooperation. The holes can simply be sized to accept and retain the bar-like magnetic masses. For example, a press fit or interference fit of the bar-like masses of magnetic material into the respective holes may be sufficient for this purpose. In this case, the bar-like masses would extend toward but short of one another from the leaflets so that magnetic flux from the magnet (or between opposite magnetic poles if both magnetic masses are magnets) magnetically couple to the masses together. The length of the bar-like magnetic masses extending toward one another from the leaflets would provide the necessary lever arm so that the magnetic coupling between distal ends of the bar-like masses provides a torque interaction for the leaflets like that described above. Accordingly, the present invention is intended to be limited only by the spirit and scope of the appended claims, which also provide a definition of the invention.

I claim:

1. A mechanical prosthetic valve for human implantation, said valve comprising:

a base portion defining a blood flow pathway therethrough;

a pair of valve leaflets pivotally disposed in said blood flow pathway and responsive to blood fluid pressure to pivot between a first position of occluding cooperation both with one another and with said base portion to inhibit blood flow in said pathway, and a second fully open pivotal position opening blood flow in said pathway; and means for yieldably biasing said pair of valve leaflets both from said first position and from said second position toward a third pivotal position intermediate of said first and said second pivotal positions, wherein said third position for said pair of valve leaflets is angularly about half way between said first and second pivotal positions.

2. The mechanical prosthetic valve of claim 1 wherein said third pivotal position is a dynamically stable position for said valve leaflets.

3. The mechanical prosthetic valve of claim 1 wherein said means for yieldably biasing said pair of valve leaflet comprises magnetic members in each leaflet which are positioned to interact to bias the leaflets away from both said first position and said second position.

4. The mechanical prosthetic valve of claim 1 further including means for drivingly interconnecting said pair of leaflets for pivotal motion in true pivotal symmetry between said first and said second positions.

5. The mechanical prosthetic valve of claim 4 wherein said means for drivingly interconnecting said pair of leaflets for pivotal motion in symmetry between said first and said second positions includes each of said pair of leaflets including a semi-circular baffle portion extending toward the other of said pair of leaflets, each of said baffle portions defining an edge surface having a gear-tooth sector, said gear-tooth sectors of said baffle portions drivingly engaging one another to pivot said pair of leaflets in symmetry between said first and said second positions.

6. The mechanical prosthetic valve of claim 1 wherein each of said pair of valve leaflets includes both a first edge surface and a second edge surface, in said first position of said pair of valve leaflets said first edge surfaces sealingly cooperating with one another and said second edge surfaces sealingly cooperating with an interior surface of said base portion, in said second position of said pair of valve leaflets said first edge surfaces being spaced from one another and said second edge surfaces being spaced from said interior surface of said base portion.

7. The mechanical prosthetic valve of claim 1 further including each of said pair of valve leaflets defining a respective pivot axis in cooperation with said base portion and about which each valve leaflet pivots between its first and second positions, each of said pair of valve leaflets further including a respective connection feature which is spaced from said pivot axis and angularly disposed at a selected angle relative to said valve leaflet, and said means for yieldably biasing said pair of valve leaflets to a third pivotal position intermediate of said first and said second pivotal positions including a resilient member extending between and interconnecting said connection features of said pair of valve leaflets to bias the latter to said third position.

8. The mechanical prosthetic valve of claim 7 wherein said resilient member includes a coil tension spring extending between and interconnecting said pair of valve leaflets at said connection features thereof.

9. The mechanical prosthetic valve of claim 7 wherein said connection features includes each of said pair of valve leaflets carrying a respective pin having an end portion positioned angularly relative to each said leaflets and also spaced radially from said pivot axis of each said leaflet, said means for yieldably biasing said pair of leaflets to said third pivotal position interconnecting with said pair of leaflets at said end portions of respective ones of said pins.

10. The mechanical prosthetic valve of claim 1 wherein each one of said pair of valve leaflets in said third position thereof is angularly positioned at a like angle from one of said first and second pivotal positions therefor.

11. The mechanical prosthetic valve of claim 1 wherein each of said pair of valve leaflets defines a respective pivot axis in cooperation with said base portion and about which each valve leaflet pivots between its first and second positions, said means for yieldably biasing said pair of valve leaflets to a third pivotal position intermediate of said first and said second pivotal positions includes each of said pair of valve leaflets further including one of a pair of magnetic masses attracting one another, said pair of magnetic masses being angularly disposed relative to each respective valve leaflet so as to be aligned with one another along a line between said pivot axes in said third position of said valve leaflets.

12. The mechanical prosthetic valve of claim 11 wherein each one of said pair of magnetic masses includes a magnet.

13. The mechanical prosthetic valve of claim 11 wherein one of said pair of magnetic masses includes a magnet, the other of said pair of magnetic masses including a magnetic material.

14. The mechanical prosthetic valve of claim 11 wherein one of said pair of magnetic masses includes a bar-like magnet having a pair of opposite magnetic poles, said pair of opposite magnetic poles being aligned along a radial line from said pivot axis of the one of said pair of valve leaflets carrying said bar-like magnet so that one of said pair of magnetic poles is spaced from said pivot axis.

15. The mechanical prosthetic valve of claim 14 wherein said one magnetic pole is oriented radially outwardly from said pivot axis for the valve leaflet carrying said magnet.

16. The mechanical prosthetic valve of claim 11 wherein each one of said pair of magnetic masses includes a bar-like magnet having a first magnetic pole and a magnetically-opposite second magnetic pole, each bar-like magnet being carried by a respective one of said pair of valve leaflets so that said magnetic poles of said bar-like magnet align along a respective radial line from said pivot axis, on each of said pair of valve leaflets a magnetically-opposite pole being disposed radially outwardly so that said magnetically-opposite poles are spaced from the respective pivot axis, confronting and attracting one another, and in said third position of said valve leaflets are aligned along a line extending between said pivot axes.

17. The mechanical prosthetic valve of claim 11 wherein one of said pair of magnetic masses includes a bar-like magnet having a first magnetic pole and an opposite second magnetic pole, said first and second magnetic poles being aligned along a line substantially parallel with and spaced from said pivot axis for the one of said pair of valve leaflets carrying said bar-like magnet, in a view parallel with said pivot axis said bar-like magnet being disposed angularly relative to said one valve leaflet to lie on a line extending between said pivot axes when said one valve leaflet is in said third pivotal position and is intermediate of said first and said second pivotal positions.

18. The mechanical prosthetic valve of claim 17 wherein each one of said pair of magnetic masses includes a bar-like magnet having a respective first magnetic pole and an opposite second magnetic pole, each one of said pair of opposite magnetic poles being aligned along a respective line substantially parallel with and spaced from the respective pivot axis, said bar-like magnets each being disposed at a position angulated relative to the respective valve leaflet so that in said third position thereof and in a view parallel with said pivot axes, opposite magnetic poles are positioned to lie on a line extending between said pivot axes.

19. The mechanical prosthetic valve of claim 11 wherein one of said pair of magnetic masses includes a bar-like magnet having a first magnetic pole and an opposite second magnetic pole, said opposite magnetic poles being aligned along a line substantially parallel with and spaced from said pivot axis of the one of said pair of valve leaflets carrying said bar-like magnet, in a view parallel with the respective pivot axis said bar-like magnet being disposed angularly relative to said one valve leaflet to lie on a line extending between said pivot axes in said third position of said valve leaflets; the other of said pair of magnetic masses also being of bar-like configuration to be aligned along a line substantially parallel with and spaced from the respective pivot axis of the other of said pair of valve leaflets, said bar-like magnetic mass in a view parallel with said pivot axes also being disposed angularly relative to said other valve leaflet to lie on a line extending between said pivot axes in said third position of said valve leaflets.

20. The mechanical prosthetic valve of claim 1 wherein said valve includes said pair of valve leaflets and further includes a third valve leaflet, each one of said pair of leaflets and said third leaflet occluding substantially 120 degrees of said blood flow pathway.

21. The mechanical prosthetic heart valve of claim 20 wherein each one of said pair of leaflets and said third valve leaflet is provided with a means for carrying a magnetic mass, each means for carrying confronting a means for carrying of a next-adjacent one of said leaflets, each means for carrying one of a respective pair of confronting magnetic masses, and said pair of magnetic masses attracting one another to bias all of said valve leaflets to said third position.

22. The mechanical prosthetic heart valve of claim 21 wherein each one of said means for carrying a magnetic mass comprises a projection from the individual one of said leaflets toward the next adjacent one of said leaflets.

23. A method of making a mechanical prosthetic heart valve, said method comprising steps of:

providing a base portion defining a blood flow pathway therethrough;

providing a pair of fluid pressure responsive valve leaflets;

disposing said a pair of valve leaflets in said blood flow pathway and pivoting said pair of leaflets in response to blood fluid pressure between a first position of sealing cooperation both with one another and with said base portion to occlude blood flow in said pathway, and a filly open second position in which said leaflets open blood flow through said pathway; and yieldably biasing said pair of valve leaflets to a dynamically stable third pivotal position about half-way between said first pivotal position and said second pivotal position.

24. The method of claim 23, further including the step of coupling the pivoting motion of said pair of leaflets to ensure synchronous motion between said first pivotal position and said second pivotal position.

25. The method of claim 23 further including the step of using a pair of magnetic masses carried one on each one of said pair of valve leaflets and attracting one another to yieldably bias said leaflets to said third position.

26. The method of claim 25 further including the step of using a permanent magnet as one of said pair of magnetic masses.

27. The method of claim 23 further including the additional steps of:

providing each one of said pair of valve leaflets with a projection from the leaflet toward an adjacent leaflet; and arranging said pair of valve leaflets in said blood flow pathway so that said projections of adjacent leaflets confront one another;

providing a pair of magnetic masses carried one on each one of said pair of valve leaflets at said projection; and attracting said pair of magnetic masses to one another to yieldably bias said pair of valve leaflets pivotally to said third position.

28. A method of operating a mechanical prosthetic valve in association with a heart which during a pumping stroke provides pulsatile blood flow, said valve including a base portion defining a blood flow pathway therethrough, a pair of fluid pressure responsive valve leaflets pivotally disposed in said blood flow pathway and pivoting in response to blood fluid pressure between a first position and a fully open second position, in said first position said pair of valve leaflets sealingly cooperating both with one another and with said base portion to occlude said blood flow pathway, and in said second pivotal position said pair of valve leaflets being pivoted out of sealing cooperation with one another and said base portion to open blood flow via said pathway; said method comprising steps of:

yieldably biasing said pair of valve leaflets to a dynamically stable third pivotal position intermediate of said first and second positions; and using said yieldable bias to provide an anticipatory closing of said pair of valve leaflets from said second position toward said third position substantially at an end of said pumping stroke.

29. A method of operating a mechanical prosthetic valve in association with a heart which during a pumping stroke provides pulsatile blood flow, said valve including a base portion defining a blood flow pathway therethrough, a pair of fluid pressure responsive valve leaflets pivotally disposed in said blood flow pathway and pivoting in response to blood fluid pressure between a first position and a fully open second position, in said first position said pair of valve leaflets sealingly cooperating both with one another and with said base portion to occlude said blood flow pathway, and in said second pivotal position said pair of valve leaflets being pivoted out of sealing cooperation with one another and said base portion to open blood flow via said pathway; said method comprising steps of:

providing a pair of magnetic masses carried one on each of said pair of valve leaflets;

using mutual attraction of said magnetic masses for one another to yieldably bias said pair of valve leaflets to a dynamically stable third pivotal position intermediate of said first and second positions; and using said yieldable bias to provide an anticipatory closing of said pair of valve leaflets from said second position toward said third position substantially at an end of said pumping stroke.

30. A mechanical prosthetic heart valve comprising:

an annular base portion defining a blood flow pathway therethrough;

a pair of masses formed of magnetic material; and a pair of valve leaflets pivotally disposed in said blood flow pathway and each pivoting about a respective pivot axis in response to blood fluid pressure between a first pivotal position of sealing cooperation with one another and said base portion to occlude blood flow in a first direction, and a second pivotal position in which said valve leaflets are spaced apart to open blood flow in an opposite second direction, each one of said pair of valve leaflets carrying a respective one of said pair of masses, at least one of said pair of masses having a magnetic pole thereof disposed to provide magnetic flux linking the pair of masses in mutually attracting relation, and each of said pair of masses being spaced from the respective pivot axis of the valve leaflet carrying each mass to swing in a respective arc as the valve leaflet pivots, said respective arcs being juxtaposed so that each valve leaflet of said pair magnetically affects and exerts a torque on the other to cooperatively bias the pair of valve leaflets to a dynamically stable third pivotal position intermediate of said first and second positions.

31. The mechanical prosthetic heart valve of claim 30 wherein said valve includes three valve leaflets each occluding substantially 120 degrees of said blood flow pathway in plan view of said valve.

32. The mechanical prosthetic heart valve of claim 31 wherein one of said pair of masses comprises a permanent magnet.

33. A mechanical prosthetic valve for human implantation, said valve comprising:

a base portion defining a blood flow pathway therethrough;

a pair of valve leaflets pivotally disposed in said blood flow pathway, each of said pair of valve leaflets being pivotal about a respective pivot axis and pivoting in response to blood fluid pressure between a first position of occluding cooperation both with one another and with said base portion to inhibit blood flow in said pathway, and a second fully open pivotal position opening blood flow in said pathway; and means for yieldably biasing said pair of valve leaflets both from said first position and from said second position toward a third pivotal position intermediate of said first and said second pivotal positions, said means for yieldably biasing said pair of valve leaflets including each one of said pair of valve leaflets carrying a respective one of a pair of magnetic masses, at least one of said pair of masses providing magnetic flux linking the pair of magnetic masses in mutually attracting relation, and each of said pair of masses being spaced from the respective pivot axis of the valve leaflet carrying each respective magnetic mass so as to swing in a respective arc as the valve leaflet pivots, these respective arcs being juxtaposed along a line perpendicular to said pivot axes so that each valve leaflet magnetically affects and exerts a torque on the other to cooperatively bias the pair of valve leaflets to said dynamically stable third pivotal position.

34. A method of operating a mechanical prosthetic valve in association with a heart which during a pumping stroke provides pulsatile blood flow, said valve including a base portion defining a blood flow pathway therethrough, a pair of fluid pressure responsive valve leaflets pivotally disposed in said blood flow pathway and pivoting in response to blood fluid pressure between a first position and a fully open second position, in said first position said pair of valve leaflets sealingly cooperating both with one another and with said base portion to occlude said blood flow pathway, and in said second pivotal position said pair of valve leaflets being pivoted out of sealing cooperation with one another and said base portion to open blood flow via said pathway; said method comprising steps of:

yieldably biasing said pair of valve leaflets both from said first pivotal position and from said second pivotal position to a dynamically stable third pivotal position intermediate of said first and second positions; and using said yieldable bias to provide an anticipatory opening of said pair of valve leaflets from said first position toward said third position in response to a substantially balanced blood pressure on opposite sides of said pair of valve leaflets.

35. The method of claim 34 including the step of using said yieldable bias to also provide an anticipatory closing of said pair of valve leaflets from said second position toward said third position substantially at an end of said pumping stroke.

36. A method of operating a mechanical prosthetic valve in association with a heart which during a pumping stroke provides pulsatile blood flow, said valve including a base portion defining a blood flow pathway therethrough, a pair of fluid pressure responsive valve leaflets pivotally disposed in said blood flow pathway and pivoting in response to blood fluid pressure between a first position and a fully open second position, in said first position said pair of valve leaflets sealingly cooperating both with one another and with said base portion to occlude said blood flow pathway, and in said second pivotal position said pair of valve leaflets being pivoted out of sealing cooperation with one another and said base portion to open blood flow via said pathway; said method comprising steps of:

yieldably biasing said pair of valve leaflets both from said first pivotal position and from said second pivotal position to a dynamically stable third pivotal position intermediate of said first and second positions; and biasing said pair of valve leaflets toward synchronous pivotal movement as said pair of valve leaflets pivot between said first and said second positions using said yieldable bias toward said third position.

37. A mechanical prosthetic valve for human implantation, said valve comprising:

a base portion defining a blood flow pathway therethrough;

a pair of valve leaflets pivotally disposed in said blood flow pathway and responsive to blood fluid pressure to pivot between a first position of occluding cooperation both with one another and with said base portion to inhibit blood flow in said pathway, and a second fully open pivotal position opening blood flow in said pathway; and means for yieldably biasing said pair of valve leaflets both from said first position and from said second position toward a third pivotal position intermediate of said first and said second pivotal positions, wherein each of said pair of valve leaflets defines a respective pivot axis in cooperation with said base portion and about which each valve leaflet pivots between its first and second positions, said means for yieldably biasing said pair of valve leaflets to a third pivotal position intermediate of said first and said second pivotal positions includes each of said pair of valve leaflets further including one of a pair of magnetic masses attracting one another, said pair of magnetic masses being angularly disposed relative to each respective valve leaflet so as to be aligned with one another along a line between said pivot axes in said third position of said valve leaflets.

38. The mechanical prosthetic valve of claim 37 wherein each one of said pair of magnetic masses includes a magnet.

39. The mechanical prosthetic valve of claim 37 wherein one of said pair of magnetic masses includes a magnet, the other of said pair of magnetic masses including a magnetic material.

40. The mechanical prosthetic valve of claim 37 wherein one of said pair of magnetic masses includes a bar-like magnet having a pair of opposite magnetic poles, said pair of opposite magnetic poles being aligned along a radial line from said pivot axis of the one of said pair of valve leaflets carrying said bar-like magnet so that one of said pair of magnetic poles is spaced from said pivot axis.

41. The mechanical prosthetic valve of claim 37 wherein said one magnetic pole is oriented radially outwardly from said pivot axis for the valve leaflet carrying said magnet.

42. The mechanical prosthetic valve of claim 37 wherein each one of said pair of magnetic masses includes a bar-like magnet having a first magnetic pole and a magnetically-opposite second magnetic pole, each bar-like magnet being carried by a respective one of said pair of valve leaflets so that said magnetic poles of said bar-like magnet align along a respective radial line from said pivot axis, on each of said pair of valve leaflets a magnetically-opposite pole being disposed radially outwardly so that said magnetically-opposite poles are spaced from the respective pivot axis, confronting and attracting one another, and in said third position of said valve leaflets are aligned along a line extending between said pivot axes.

43. The mechanical prosthetic valve of claim 37 wherein one of said pair of magnetic masses includes a bar-like magnet having a first magnetic pole and an opposite second magnetic pole, said first and second magnetic poles being aligned along a line substantially parallel with and spaced from said pivot axis for the one of said pair of valve leaflets carrying said bar-like magnet, in a view parallel with said pivot axis said bar-like magnet being disposed angularly relative to said one valve leaflet to lie on a line extending between said pivot axes when said one valve leaflet is in said third pivotal position and is intermediate of said first and said second pivotal positions.

44. The mechanical prosthetic valve of claim 43 wherein each one of said pair of magnetic masses includes a bar-like magnet having a respective first magnetic pole and an opposite second magnetic pole, each one of said pair of opposite magnetic poles being aligned along a respective line substantially parallel with and spaced from the respective pivot axis, said bar-like magnets each being disposed at a position angulated relative to the respective valve leaflet so that in said third position thereof and in a view parallel with said pivot axes, opposite magnetic poles are positioned to lie on a line extending between said pivot axes.

45. The mechanical prosthetic valve of claim 37 wherein one of said pair of magnetic masses includes a bar-like magnet having a first magnetic pole and an opposite second magnetic pole, said opposite magnetic poles being aligned along a line substantially parallel with and spaced from said pivot axis of the one of said pair of valve leaflets carrying said bar-like magnet, in a view parallel with the respective pivot axis said bar-like magnet being disposed angularly relative to said one valve leaflet to lie on a line extending between said pivot axes in said third position of said valve leaflets; the other of said pair of magnetic masses also being of bar-like configuration to be aligned along a line substantially parallel with and spaced from the respective pivot axis of the other of said pair of valve leaflets, said bar-like magnetic mass in a view parallel with said pivot axes also being disposed angularly relative to said other valve leaflet to lie on a line extending between said pivot axes in said third position of said valve leaflets.

46. A method of making a mechanical prosthetic heart valve, said method comprising steps of:

providing a base portion defining a blood flow pathway therethrough;

providing a pair of fluid pressure responsive valve leaflets;

disposing said a pair of valve leaflets in said blood flow pathway and pivoting said pair of leaflets in response to blood fluid pressure between a first position of sealing cooperation both with one another and with said base portion to occlude blood flow in said pathway, and a fully open second position in which said leaflets open blood flow through said pathway; and yieldably biasing said pair of valve leaflets to a dynamically stable third pivotal position intermediate of said first and said second positions by using a pair of magnetic masses carried one on each one of said pair of valve leaflets and attracting one another to yieldably bias said leaflets to said third position.

47. The method of claim 46 further including the step of using a permanent magnet as one of said pair of magnetic masses.

48. The method of claim 46 further including the additional steps of:

providing each one of said pair of valve leaflets with a projection from the leaflet toward an adjacent leaflet; and arranging said pair of valve leaflets in said blood flow pathway so that said projections of adjacent leaflets confront one another;

providing a pair of magnetic masses carried one on each one of said pair of valve leaflets at said projection; and attracting said pair of magnetic masses to one another to yieldably bias said pair of valve leaflets pivotally to said third position.

49. A method of making a mechanical prosthetic heart valve, said method comprising steps of:

providing a base portion defining a blood flow pathway therethrough;

providing a pair of fluid pressure responsive valve leaflets;

providing each one of said pair of valve leaflets with a projection from the leaflet toward an adjacent leaflet;

disposing said pair of valve leaflets in said blood flow pathway so that said projections of adjacent leaflets confront one another, and pivoting said pair of leaflets in response to blood fluid pressure between a first position of sealing cooperation both with one another and with said base portion to occlude blood flow in said pathway, and a fully open second position in which said leaflets open blood flow through said pathway;

providing a pair of magnetic masses carried one on each one of said pair of valve leaflets at said projection; and attracting said pair of magnetic masses to one another to yieldably bias said pair of valve leaflets pivotally to a dynamically stable third pivotal position intermediate of said first and said second positions.

* * * * *